United States Patent [19]
Muller et al.

[11] Patent Number: 5,986,152
[45] Date of Patent: Nov. 16, 1999

[54] SUPPORTED CATALYST, PROCESS FOR ITS PRODUCTION AS WELL AS ITS USE IN THE OXYCHLORINATION OF ETHYLENE

[75] Inventors: Herbert Muller, Altrip; Stefan Bosing, Mainz-Kostheim; Ludwig Schmidhammer, Haiming; Albin Frank, Burghausen; Klaus Haselwarter, Emmerting, all of Germany

[73] Assignee: Degussa-Hüls AG, Frankfurt, Germany

[21] Appl. No.: 09/198,251

[22] Filed: Nov. 24, 1998

[30] Foreign Application Priority Data

Nov. 24, 1997 [DE] Germany ............... 197 51 962

[51] Int. Cl.⁶ .................... C07C 17/156; B01J 23/72
[52] U.S. Cl. .................. 570/243; 570/246; 570/247; 570/248; 502/302; 502/303; 502/304; 502/344; 502/345; 502/349
[58] Field of Search .................... 570/243, 246, 570/247, 248, 302, 303, 304, 344, 345, 349

[56] References Cited

U.S. PATENT DOCUMENTS

| | | |
|---|---|---|
| 3,914,390 | 10/1975 | Kudo et al. . |
| 4,044,068 | 8/1977 | Kurtz ............................ 585/636 |
| 4,329,323 | 5/1982 | Shiozaki et al. ............. 423/240 R |
| 4,366,093 | 12/1982 | Shiozaki et al. ............. 502/439 |
| 4,382,021 | 5/1983 | Lauer et al. ................ 502/225 |
| 4,446,249 | 5/1984 | Eden . |
| 4,849,393 | 7/1989 | Eden et al. . |
| 5,099,085 | 3/1992 | Strasser et al. ............. 570/245 |
| 5,166,120 | 11/1992 | Deller et al. ............... 502/225 |

FOREIGN PATENT DOCUMENTS

| | | |
|---|---|---|
| 0 582 165 | 2/1994 | European Pat. Off. . |
| 17 68 453 | 3/1971 | Germany . |
| 25 01 810 | 8/1975 | Germany . |
| 40 18 512 | 12/1991 | Germany . |
| WO 96/40431 | 12/1996 | WIPO . |

OTHER PUBLICATIONS

J.A. Allen and A.J. Clark, Oxychlorination Catalysts, Reviews of Pure and Applied Chemistry, Sep. 21, 1971, p. 145–166.

Database WPI, Derwent Publications Ltd., Preparation Chlorinated Hydrogen Chloride Catalyst Comprise Copper Chloride Carry Organic Porous Carry, Section CH, Week 9540 XP–002093878 (Aug. 1995).

Primary Examiner—Thomas Dunn
Attorney, Agent, or Firm—Pillsbury Madison & Sutro LLP

[57] ABSTRACT

A supported catalyst includes: a) 0.5–15 wt. % of one or more Cu-II compounds, the quantitative amounts referring to copper metal; b) 0.1–8 wt. % of one or more alkali metal compounds, the quantitative amounts referring to alkali metal; c) 0.1–10 wt. % of an oxide mixture including; c1) 80–95 mole % of oxides of cerite rare earths with atomic Nos. 57 to 62, except promethium, and c2) 5–20 mole % of zirconium dioxide, where c1) and c2) must together total 100 mole % and the quantitative amount of c) refers to the oxides of the mixture, and d) the remainder up to 100 wt. % being γ and/or α-aluminum oxide as support material, wherein e) the support material d) has a total pore volume in the range from 0.65 to 1.2 cm³/g, and wherein f) the supported catalyst is present in the form of cylindrical hollow bodies having at least one passage channel, the ratio of height h to external diameter $d^e$ being less than 1.5 for diameters $d_e$ of up to 6 mm, and the ratio $h/d_e$ being less than 0.6 for diameter $d_e$ greater than 6 mm. A process for producing the supported catalyst is also described.

19 Claims, 4 Drawing Sheets

SUPPORTED CATALYST, PROCESS FOR ITS PRODUCTION AS WELL AS ITS USE IN THE OXYCHLORINATION OF ETHYLENE

FIELD OF THE INVENTION

The present invention relates to a shaped supported catalyst for the oxychlorination of ethylene that achieves a high hydrogen chloride conversion with improved reaction selectivity at relatively low reaction temperatures and large space flow velocities and that also retains its geometrical shape and activity over a long period. The supported catalyst according to the invention contains copper ions and alkali metal ions on specially shaped aluminum oxide supports with increased pore volume, especially in the mesopore range, that are dimensionally stabilized by oxidic additives against thermal decomposition. The invention concerns a process for the production of such supported catalysts as well as the use of these supported catalysts, in particular in the selective oxychlorination of ethylene with air, with oxygen-enriched air or with pure oxygen, with cycling of ethylene-rich gas.

BACKGROUND OF THE INVENTION

The oxychlorination of ethylene is a well-known, industrially employed process that is carried out in fluidized-bed and fixed-bed reactors. Despite the more uniform temperature distribution in the reaction zone the disadvantages of the fluidized-bed process must not be overlooked, such as back-mixing and abrasion problems as well as certain difficulties in the flow behavior of the catalyst, which can lead to an agglomeration of the catalyst particles, whereby in particular the reaction selectivity is adversely affected. For example, the technological advantage of an oxygen cycled gas procedure with up to 80 vol. % of ethylene in the cycled gas, in which the released enthalpy of reaction is optimally dissipated corresponding to the present state of the best available technology, cannot be employed in a fluidized-bed oxychlorination.

On the other hand in the fixed-bed process, in which moreover the reactants can also be more accurately controlled, the oxygen cycled gas procedure can be carried out satisfactorily with a high ethylene content in the cycled gas. The suppression of the disadvantages of the fixed-bed process, such as in particular the occurrence of local temperature peaks (so-called hot spots), increased pressure drop over the reactors as well as a gradual decomposition of the shaped supported catalyst due to coke inclusions and thermally conditioned long-term effects that adversely affect the activity and selectivity as well as the catalyst life, has been the subject of numerous investigations and proposed improvements that have been disclosed in the literature, such as the addition of activity-enhancing and selectivity-enhancing promoters, the addition of thermal stabilizers to the support material, the selection of flow-promoting and/or thermodynamically and reaction kinetically advantageous catalyst geometries and porosities and technical improvements by adopting the so-called multireactor technology by splitting up the hydrogen chloride and/or air and/or oxygen into the individual reactors connected in series, with and without cycling of the gas.

The following printed specifications have been named as part of the particular prior art:

Allen, J. A., Clark, A. J., Rev. Pure and Appl. Chem. 21, 148 (1971)=D1
DE-A-17 68 453=D2;
Allen, J. A., Clark A. J., J. Appl. Chem., 26, 327 (1966)=D3;
DE-A-20 50 061=D4;
U.S. Pat. No. 4,446,249=D5;
FR-2021986=D6;
Dotson, R. L., J. Catalysis 33, 210 (1974)=D7;
Villadsen, J., Livbjerg, H., Catal. Rev. Sci. Eng. 17 (2), 203 (1978)=D8;
Shatchortswa, G. A. et al., Kinet, i Katal. 11, 1224 (1970)=D9;
Ruthren, D. M., Kennedy, C. N., J. Inorg. Nucl. Chem 30, 931 (1965)=D10;
Dirksen, F., Chemie-Technik 12 (1983) No. 6, 36–43= D11;
EP-A-0 582 165=D12;
EP-A-0 775 522=D13; and
WO 96/40431=D14.

D1 discloses a large number of promoters and activators, such as the oxides and/or chlorides of lanthanum, platinum, zirconium, uranium, cerium, thorium, titanium, tantalum, rhodium, molybdenum, ruthenium, tungsten, europium as well as didymium mixtures of rare earth metals, which in some cases are said to favorably influence the pure Deacon reaction as well as the oxychlorination reaction.

D2 describes a fluidized-bed oxychlorination catalyst based on silica as support, which in addition to copper chloride and alkali metal chloride contains, besides chlorides of the rare earths or chlorides of scandium, zirconium, thorium and uranium, also yttrium chloride. Although yttrium-III chloride reacts with oxygen with the release of chlorine and formation of $Y_2O_3$, a gas-impermeable oxide film is formed however (D3). The system $YCl_3/Y_2O_3$ is thus not very suitable for the fixed-bed catalyst since on account of the film-like oxide coating the catalyst surface agglomerates and the rate of reaction between $YCl_3$ and oxygen very rapidly decreases. In the fluidized-bed process on the other hand there is a mechanical destruction of the film-like oxide coating due to the constant mutual friction of the catalyst particles.

D4 claims a supported catalyst for the fluidized-bed or fixed-bed oxychlorination, which in addition to copper chloride also contains compounds of the rare earth metals with atomic No. 62 and above and/or compounds of yttrium on active aluminum oxide as support material. In contradiction to D2, the presence of alkali metals is deleterious since they reduce the activity of the catalysts.

According to D5 and D6 additives of compounds of the rare earth metals, in particular compounds of lanthanum, are used in the fluidized-bed process in order to prevent an agglomeration of the fluidized-bed catalyst particles.

The same effect of the lanthanide metal compounds is described by R. L. Dotson in D7.

According to D8 however lanthanum-III chloride increases the sublimation rate of copper chloride/potassium chloride systems, as a result of which such catalysts lose their activity over time.

In D9 it is assumed that lanthanum, on account of its strong complex-forming tendency, removes chloride ions from the copper chloride/potassium chloride system, whereupon the potassium/copper chlorocomplex becomes depleted in chloride and thus the copper chloride volatility is increased.

According to D10 the activating effect of lanthanum-III chloride is based only on an increase in the pre-exponential frequency factor in the Arrhenius equation, without reducing the activation energy, since it accelerates the velocity-determining re-oxidation of the copper-I species that is formed as intermediate. Since this frequency factor is however considerably less dependent on temperature than the reaction velocity constant k, the catalytic effect of lanthanum-III chloride is overall weaker.

In order to improve the temperature stability and thermal resistance of an oxychlorination catalyst based on gamma-aluminum oxide as support, i.e. in order to increase its resistance to elevated temperatures during its useful life without altering the physical structure of the transitional alumina matrix, there are used inter alia additives of lanthanum oxide or thorium oxide (D11) and other oxides of the rare earth metals (D4), though of course it is the hydrated aluminum oxide, which is used to obtain the activated aluminum oxide, that is of decisive importance for the temperature stability of the resultant porous solid. The gamma-aluminum oxide obtained by boehmite dehydration is most stable as regards heat treatment, in which connection during the action of elevated temperatures under hydrothermal conditions of an oxychlorination reaction there is a gradual conversion during the use of the gamma-aluminum oxide to the catalytically inactive but thermodynamically stable alpha-aluminum oxide, presumably after partial rehydration to boehmite and diaspore (equilibrium) which already at 420° C. transforms into alpha-aluminum oxide, whereas by thermal decomposition of gamma-aluminum oxide alpha-aluminum oxide is formed only at 1000° C. The gamma-aluminum oxide that crystallizes in the tetragonal spinel form is converted into hexagonal rhombohedral alpha-aluminum oxide. This change in the physical structure and morphology leads to a gradual disintegration of the shaped catalyst particles, whereby the pressure drop can increase over the reactor packing right up to the bed compaction, and on account of the different disintegration rates the gas distribution over the reactor cross-section becomes increasingly less uniform. Both these effects result in the catalyst having to be replaced prematurely.

In addition it is known that the mechanical strength of supported catalysts depends on their geometry and porosity, in which connection it is fairly generally accepted that thick-wall support geometries with large diameters and supports with a relatively small pore volume are mechanically most stable.

D12 discloses a catalyst and a process for the oxychlorination of ethylene to dichloroethane; the catalyst comprises a support that has an active metal composition comprising 2 to 8 wt. % of copper as chloride, or in the form of other copper salts, 0.2 to 2 wt. % of an alkali metal (alkali metals), 0.1 to 9 wt. % of a rare earth metal (rare earth metals) and 0.05 to 4 wt. % of a metal (metals) of Group IIA of the Periodic System of the Elements (IUPAC 1970), all percentages by weight being referred to the total weight of the catalyst composition, wherein all metals are deposited on the support and the catalyst composition has a specific surface in the range from 20 to 220 m²/g. The support is aluminum oxide with a bulk density in the range from 0.8 to 1.1 g/cm³ and a pore volume of between 0.2 and 0.5 ml/g.

D13 discloses catalysts for the oxychlorination of ethylene in the form of hollow cylindrical granules having at least three passage channels. A production process is disclosed in which catalysts are formed having a fairly large porosity and a fairly narrow pore radius distribution. The porosity is in the range from 0.2 to 0.5 cm³/g, while the BET surface is in the range from 80 to 380 m²/g. D14 is similar, and discloses car wheel-shaped catalysts for the oxychlorination.

It has however been shown that the previously specified instructions and assumptions, which to some extent are contradictory, are overall incapable of achieving fully all the demands placed on supported catalysts.

SUMMARY OF THE INVENTION

Having regard to the aforedescribed and discussed prior art, there was therefore the need to provide a supported catalyst for the oxychlorination of ethylene that exhibits an improved activity.

A further object of the invention is to provide a supported catalyst for the oxychlorination of ethylene that exhibits an improved selectivity.

Yet another object is to provide a supported catalyst for the oxychlorination of ethylene having improved temperature stability, in particular against local overheating.

The object of the invention is moreover to improve the activity, selectivity and temperature stability, in particular against local overheating, of the hitherto known supported catalysts for the oxychlorination of ethylene in order to obtain with flow-promoting and thermodynamically advantageous, for example reaction kinetically advantageous, geometries and porosities, an improved combination of properties, compared to the supported catalysts of the prior art, of the supported catalysts according to the invention as regards long-term activity, selectivity and dimensional stability.

In addition the object of the invention is to provide a simple and readily realizable process for producing a supported catalyst having improved activity, selectivity, temperature stability and/or improved long-term stability of the activity, selectivity and/or dimensional stability.

Finally, the invention also relates to the use of improved supported catalysts.

A whole series of advantages can be combined in a manner that was not directly foreseeable, by the use of a supported catalyst characterized in that it contains:
 a) 0.5–15 wt. % of one or more Cu-II compounds, the quantitative amounts referring to copper metal,
 b) 0.1–8 wt. % of one or more alkali metal compounds, the quantitative amounts referring to alkali metal,
 c) 0.1–10 wt. % of an oxide mixture comprising
  c1) 80–95 mole % of oxides of cerite rare earths with atomic Nos. 57 to 62, except promethium, and
  c2) 5–20 mole % of zirconium dioxide, where c1) and c2) must together total 100 mole % and the quantitative amount of c) refers to the oxides of the mixture, and
 d) the remainder up to 100 wt. % being γ- and/or α-aluminum oxide as support material, wherein
 e) the support material d) has a total pore volume in the range from 0.65 to 1.2 cm³/g, and wherein
 f) the supported catalyst is present in the form of cylindrical hollow bodies having at least one passage channel, the ratio of height h to external diameter $d_e$ being less than 1.5 for diameters $d_e$ of up to 6 mm, and the ratio $h/d_e$ being less than 0.6 for diameter $d_e$ greater than 6 mm.

The supported catalyst according to the invention exhibit or permit:
 low pressure losses;
 low bulk densities;
 relatively large external surfaces per unit volume of a reactor vessel;
 uniform flow through the passage channel or channels;
 generation of high reaction gas turbulences in the interior of the catalyst moldings;
 generation of high reaction gas turbulences around the shaped catalyst bodies;

increase in the axial and radial mixing, in other words mass transport against the flow direction under the influence of a concentration gradient;

enhancement and facilitation of the diffusion capacity of the gaseous reactants in the channels;

enhancement and facilitation of the gaseous reactants in the catalyst pores as a result of mesopore dominance;

high turbulences of the reaction gases at the catalyst moldings and in the reaction space ameliorate the disadvantageous heat dissipation problems that occur on account of reduced heat exchange coefficients between the catalyst moldings and reaction gases;

achievement of higher space-time yields;

increase in conversion;

increase in selectivity;

increase in catalyst service life.

The following effects in particular should be highlighted as surprising for the person skilled in the art:

It is known that a high degree of porosity reduces the catalytically active mass per unit reaction volume. It was therefore completely unexpected that specifically the catalyst geometries according to the invention, despite their relatively large geometric surface per reactor packing volume but on the other hand very high geometrically conditioned degree of porosity, contribute together with the remaining features of the invention to an increase in activity during oxychlorination.

The temperature-stabilizing action of oxidic additives of cerite rare earth metals alone is only slightly effective under oxychlorination conditions. An addition of zirconium dioxide alone is completely ineffective. It was therefore also unexpected that an improvement in the activity and selectivity as well as dimensional stability and thermal stability under prolonged active use is nevertheless achieved with the supported catalyst according to the invention.

The increase in the activity and selectivity with at the same time an improvement in the dimensional stability and thermal stability under oxychlorination conditions is found only if supported catalysts exhibit all the features of claim 1. All claimed parameters must be simultaneously present in order clearly to overcome the already mentioned disadvantages of the individual parameters by the combination of features according to the invention, so as finally to achieve an increase, unexpected by the person skilled in the art, in the activity and selectivity as well as in the dimensional stability and thermal stability, which moreover are maintained over a long period of time. The temperature stability of the claimed catalyst moldings for example already deteriorates considerably if the supported catalyst has, deviating from the combination of features according to the invention, a total pore volume of only 0.5 cm$^3$/g.

The supported catalyst according to the invention is based on γ- and/or α-aluminum oxide as support material. These aluminum oxide modifications are well known to the person skilled in the art, and are commercially obtainable and thus accessible. The support material d) may be γ-$Al_2O_3$, α-$Al_2O_3$ or a mixture of these two modifications of $Al_2O_3$. In a suitable variant the supported catalyst of the invention is characterized by the fact that the support material d) is γ-$Al_2O_3$. The proportion of the support material d) in the supported catalyst of the invention is calculated so that the components a)–d) together total 100 wt. %. Normally the proportion of the support material d) calculated with respect to aluminum oxide is in the range between 76 and 99.3 wt. %. Amounts in the range from 78 to 95 wt. % are preferred. More preferably, the proportion is between 79 and 90 wt. %. Particularly preferred is the range between 85 and 94.5 wt. %. Even more particularly preferred is the range 87.5 to 92.5 wt. %.

The supported catalyst according to the invention contains as component c) an oxide mixture. This oxide mixture serves to modify and improve the properties of the support material d). The oxide mixture c) is contained in the supported catalyst according to the invention in an amount in the range from 0.1 to 10 wt. %, referred to the total weight of the components a) to d). The proportion of the component c) contained in the supported catalyst a) to d) is preferably in the range from 0.5 to 10 wt. %, more preferably in the range 2 to 8 wt. %, particularly preferably 3 to 7 wt. %, and most particularly 5 to 6 wt. % (in each case weight by weight).

The component c) is a mixture of the components c1) and c2). The component c2) is zirconium dioxide. The component c1) is one or more cerite earth oxides of elements with the atomic No. 57 to 62 (except promethium, with the atomic No. 61). Oxides that serve as component c2) are accordingly those of lanthanum, cerium, praseodymium, neodymium and/or samarium.

Of the above oxides, those of lanthanum, cerium and/or samarium are preferred as component c2). Particularly preferred are oxides of cerium. Most particularly preferred as the component c2) is cerium dioxide. The ratio of the components c1) to c2) may vary over a relatively wide range. The component c) conveniently comprises 80–95 mole % of c1) and 5–20 mole % of c2), the quantitative amounts of c1) and c2) referring to the molar ratios of the oxides, and c1) and c2) should be chosen so that they together total 100 mole %.

In a preferred embodiment the supported catalyst of the invention is characterized in that the oxide mixture c) comprises 80–90 mole % of c1) and 10–20 mole % of c2).

More preferably, the supported catalyst according to the invention is characterized in that the oxide mixture c) comprises 88–90 mole % of c1) and 10–12 mole % of c2). Particularly advantageous supported catalysts are obtained within the scope of the invention if 5 to 6 wt. % of a cerium dioxide/zirconium dioxide mixture containing 10 to 12 mole % of zirconium dioxide is added to the support material d).

The components d)=support material and c)=oxide mixture together form the support of the supported catalyst according to the invention.

The supported catalyst according to the invention contains, as further essential constituent a), 0.5–15 wt. %, referred to metallic copper, of one or more copper-II compounds. Copper-II compounds that may be used in the context of the invention include, inter alia, copper oxide, copper-II nitrate, sulfate, carbonate and copper halides such as copper-II bromide and/or copper-II chloride. The copper-II compounds are contained either alone or as a mixture of two or more compounds in the supported catalyst of the invention. Of the afore-mentioned copper-II compounds, copper-II halides are preferred. Especially preferred is copper-II chloride. Preferred amounts of the component a) are in the range from about 1–12 wt. %, 2–14 wt. %, 3–13 wt. %, 4–8 wt. % as well as 5–7 wt. %, in each case referred to 100 wt. % of the sum of a) to d), the component a) being calculated as metal.

In addition to the component a), it is essential that the supported catalyst according to the invention contains one or more alkali metal compounds. All ionic alkali metal compounds may be used. The alkali metal compounds that may be used as the component b) include, inter alia, the halides, preferably the bromides and chlorides, and the sulfates, carbonates and nitrates of the alkali metals, in particular the halides of potassium, sodium, rubidium and/or cesium. Potassium and/or sodium chlorides are preferably used. Of particular interest are supported catalysts in which the alkali metal compound is KCl.

The component b) is contained in the supported catalyst of the invention in an amount of 0.1 to 8 wt. %, here too, as in the case of the component a), the quantitative amount referring to the alkali metal. Preferred are amounts in the range from 0.2 to 5 wt. %, 0.4 to 3 wt. %, 0.5 to 5 wt. %, and 1 to 4 wt. %. Particularly preferred are amounts of 1.5 to 2.5 wt. %, in each case calculated as metal and always referred to the total weight of the components a) to d).

Particularly important supported catalysts according to the invention are characterized by the fact that the molar ratio of Cu-II compounds a) to alkali metal compounds b) is in the range from 1:1 to 8:1. Preferred ratios are in the range from 1:1 to 6:1, and particularly preferred are ratios in the range from 1.5:1 to 5:1, from 2:1 to 5:1, and from 2.5:1 to 4:1. In the oxychlorination the reactors have purposefully been subdivided into various zones, in which catalysts are used having active mass loads that increase in the flow direction. In this connection it may be preferred to use particular ratios of a) to b). For example, in a first variant it is preferred to use a):b) ratios of 1:1 to about 1.5:1. In a second variant a):b) ratios of between 1.5:1 to about 3:1 are used. A further variant is characterized by a):b) ratios in the range from 5:1 to 8:1, while yet another variant uses a):b) ratios of between 3:1 to about 5:1.

The components a) and b) together form the catalyst of the supported catalyst according to the invention.

The support of the supported catalyst according to the invention has a specific overall pore volume. This volume must be in the range from 0.65 to 1.2 cm$^3$/g. If the overall pore volume of the support c)+d) or also of the support material d) is less than 0.65 cm$^3$/g or greater than 1.2 cm$^3$/g, the further aforedescribed advantages achievable with the invention cannot be accomplished satisfactorily.

The support material d) or the carrier c)+d) particularly advantageously has a total pore volume in the range from 0.7 to 1.0 cm$^3$/g, preferably in the range from 0.7 to 0.9 cm$^3$/g.

The total pore volume is preferably 0.7–0.85 cm$^3$/g. As regards the pore distribution, it is preferred that 80% of the total pore volume is formed by mesopores having a diameter of 4 to 20 nm. The total pore volume is calculated from the sum of the micropore, mesopore and macropore volumes, the micropore and mesopore volumes being measured by recording nitrogen isotherms and evaluating the latter according to BET, de Boer, Barret, Joyner and Halenda, while the macropore volumes are determined by the mercury injection method.

The support, in particular the gamma-aluminum oxide support, advantageously has a specific BET surface of 150 to 250 m$^3$/g, preferably 180 to 200 m$^3$/g, the BET surface being measured according to DIN 66131.

The geometry of the supported catalyst is decisive for the success of the invention. Within the scope of the invention the supported catalysts may be in the form of cylindrical hollow bodies having at least one passage channel, wherein the ratio of height h to external diameter $d_e$ must be less than 1.5 for diameters de of up to 6 mm, and for ratios of height to external diameter of less than 0.6 must be greater than 6 mm.

The low pressure loss of the catalyst moldings according to the invention is the result of, among other things, their geometrical dimensions, which produce an extremely large free surface in the cross-section of the shaped bodies and/or a very high degree of porosity of about 0.4 to 0.5 in the catalyst packing.

Geometries that may be employed within the context of the invention include for example all hollow bodies through which fluids can flow, such as cylindrical hollow bodies, annular hollow bodies, hollow extrudates, annular hollow extrudates, wheel-shaped bodies with 2 to 12, preferably 4 to 6 spokes, and/or monolith shaped bodies. A particular supported catalyst according to the invention is in the form of a cylindrical hollow extrudate, a wheel-shaped body with 2 to 12, preferably 4 to 6 spokes, and/or a monolith body.

The external diameter of the supported catalyst geometries may vary over a wide range. Best results are achieved in principle with supported catalysts that are characterized by having external diameters in the range from 4 to 10 mm.

In the case where the supported catalysts are in the form of cylindrical hollow bodies, wheel-shaped bodies or monolith shaped bodies, it is expedient if the ratio $h/d_e$ is $\leq 0.6$, preferably $\leq 0.5$. In the case where the supported catalysts are in the form of annular extrudates, a $h/d_e$ ratio of $\leq 1.5$ is suitable, a ratio of $\leq 1$ being preferred.

The advantages of the annular hollow extrudates include comparatively low pressure losses, low bulk densities and relatively large external surfaces per unit volume of a reaction vessel. The advantages of the wheel-shaped geometry are also comparatively low pressure losses and a uniformly flow through the spaces between the spokes, and the generation of high reaction gas turbulences in the interior of the catalyst moldings as well as around the molded bodies, as a result of an increase in the axial the radial mixing, in other words mass transport against the flow direction under the influence of a prevailing concentration gradient. In the monolith shapes the advantages are similar to those of the honeycomb-shaped monoliths, and include a uniform flow in the longitudinal direction through the bilaterally open channels, which greatly increase the external surface of the catalyst support per unit volume, and an improved diffusion capability of the gaseous reactants in the channels. High turbulences of the reaction gases on the catalyst moldings and in the reaction space as is known ameliorate the heat dissipation problems that arise on account of the reduced heat exchange coefficients between the fixed-bed catalyst moldings and/or between the catalyst moldings and the reaction gas. Supports with a large free surface area in the cross-section of the moldings and/or a high degree of porosity in the packing produce as is known a low resistance to gas flow, whereby the pressure loss over the catalyst bed becomes less at comparable packing heights and thus increased space-time yields can be achieved. It is furthermore also known that a large ratio of geometric surface to volume of the shaped body increases the activity and the conversion through better contact of the reaction gases with the catalyst surface, and limits the diffusion processes of the gaseous educts in the interior of the catalyst moldings and the back-diffusion of the gaseous products from the interior of the shaped bodies, whereby the heterogeneously catalyzed oxychlorination gaseous phase reaction, which proceeds preferably and also more selectively on the more easily accessible external catalyst surface, can be more efficiently regulated.

It is also known that support materials with a relatively large total pore volume and a pore distribution predominantly in the micro and meso range increase the activity. In addition it is advantageous to use supported catalysts having as low a bulk density as possible, since less catalyst mass is thereby required per volume of predetermined reaction space.

Although the catalysts having the features a) to f) already exhibit outstanding properties, supported catalysts according to the invention can be improved still further if they contain an yttrium-III compound.

Yttrium-III oxide or chloride, preferably yttrium-III chloride, is used as the additional active component.

The oxide mixtures of cerite rare earth metals and zirconium that serve as temperature stabilizers may either be co-precipitated in hydroxide form in the aluminum hydrate precipitation process, or may be applied, after the shaping and the necessary heat treatment, together with the active components in the form of soluble cerite rare earth and/or zirconium compounds, for example as acetates, these acetates then being converted into the corresponding oxides during the subsequent calcination.

Even small additions of yttrium-III compound improve the performance of the supported catalyst according to the invention. A preferred supported catalyst of the invention is characterized in that it contains 0.5 to 10 mole % of yttrium-III compound referred to the molar content of copper-II compound(s).

Preferred amounts of yttrium-III compound are in the range from 0.5 to 5 mole %, more preferably 1 to 3 mole % and particularly preferably 1.5 to 2.5 mole %, referred to the molar content of copper-II compound.

The supported catalysts may be produced in various ways. For example, a preferred variant is characterized in that:

i) support materials d) having the geometry f) are charged with soluble precursors of the components c1) and c2);

ii) the precursor compounds are converted into the oxide form, and iii) the oxidically charged support materials are loaded with the components a) and b).

Alternatively, it may also be preferred to iv) shape a mixture of the components c) and d) into the geometry f), and v) load the shaped support materials with the components a) and b).

For example, the support may be impregnated with the active components after the shaping and a heat treatment, which latter may take place in one or more calcination stages, wherein precipitated hydrated aluminum oxide together with optionally co-precipitated cerite rare earth oxides and/or zirconium oxide that are jointly incorporated into the aluminum oxide lattice, are dehydrated.

Alternatively, the catalyst according to the invention may be obtained by primary impregnation with aqueous solutions of the cerite rare earth/zirconium salts, followed by calcination and subsequent impregnation with aqueous solutions of copper, alkali metal and optionally yttrium salts.

Again, as another alternative, a pulverulent mixture of aluminum oxide, the three active components and the oxidic temperature stabilizers may be shaped and then calcined.

The catalyst of this invention can preferably used in a fixed-bed-reactor.

The supported catalysts can clearly be used in a whole range of reactions. They are preferably used however in the oxychlorination of ethylene.

The invention also provides a process for producing 1,2-dichloroethane (EDC) by oxychlorination of ethylene with hydrogen chloride, using the supported catalyst according to the invention. Air or oxygen-enriched air, or preferably pure oxygen is used as oxidizing agent, the excess, unreacted ethylene being recycled in the ethylene-rich cycled gas. The process may be carried out in one stage or in several stages. In the preferred multi-stage reaction procedure individual constituents, for example hydrogen chloride and/or air/oxygen may be divided and added separately to each reactor. The reaction may also be carried out in a cycled gas procedure, in which the reaction mixture leaving the reaction zone is mixed with fresh hydrogen chloride, ethylene and air/oxygen and returned to the reaction zone. 1,2-dichloroethane and reaction water are separated from the reaction mixture before it is recycled. The temperatures in the catalyst packings are normally in the range between 220° C. and 300° C. at a pressure of 3 to 10 bar absolute. In the presence of the supported catalysts according to the invention 4 to 8% excess ethylene and 5 to 10% excess oxygen are sufficient, in each case referred to the stoichiometric amount of hydrogen chloride when using air, in order to achieve an almost quantitative hydrogen chloride conversion at an extremely high hydrogen chloride loading of 1.4 to 2 $Nm^3$ per liter of catalyst volume and per hour.

In the implementation of the oxychlorination process using the supported catalyst it is expedient to grade the activity of the catalyst so that the activity in the reactor in the case of a one-stage procedure or in a multi-stage procedure increases at least in the first and second stages in the product flow direction. In order to avoid diluting the catalyst with inert material, which overall has an adverse effect on the reaction, it is preferred to use copper-II chloride concentrations graded between 7.5 and 22.5 wt. % referred to the total weight of the supported catalyst, the alkali metal chloride addition likewise being graded in a molar ratio of copper-II chloride to alkali metal chloride of between 1:1 and 6:1, and in addition the yttrium-III chloride is added in amounts of between 0.5 and 5 mole %, referred to the respective molar concentration of copper-II chloride.

This application is based on German application DE 19751962.8, filed Nov. 24, 1997, which entire disclosure is incorporated herein by reference.

BRIEF DESCRIPTION OF THE DRAWINGS

The invention is illustrated in more detail hereinafter by means of exemplary embodiments and with reference to the accompanying diagrams, in which.

Figure 1:
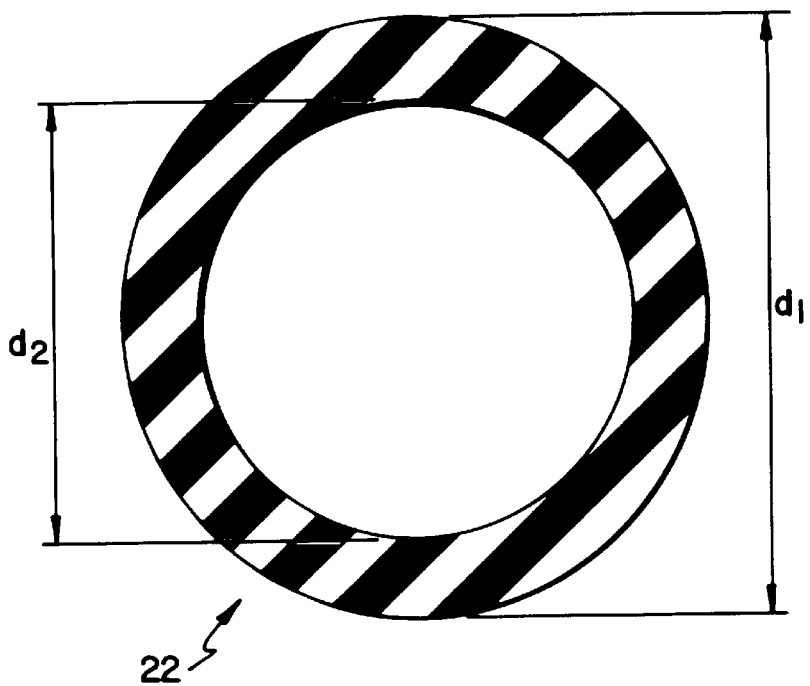
FIG. 1 is a cross-section of an annular hollow extrudate.
Figure 2:
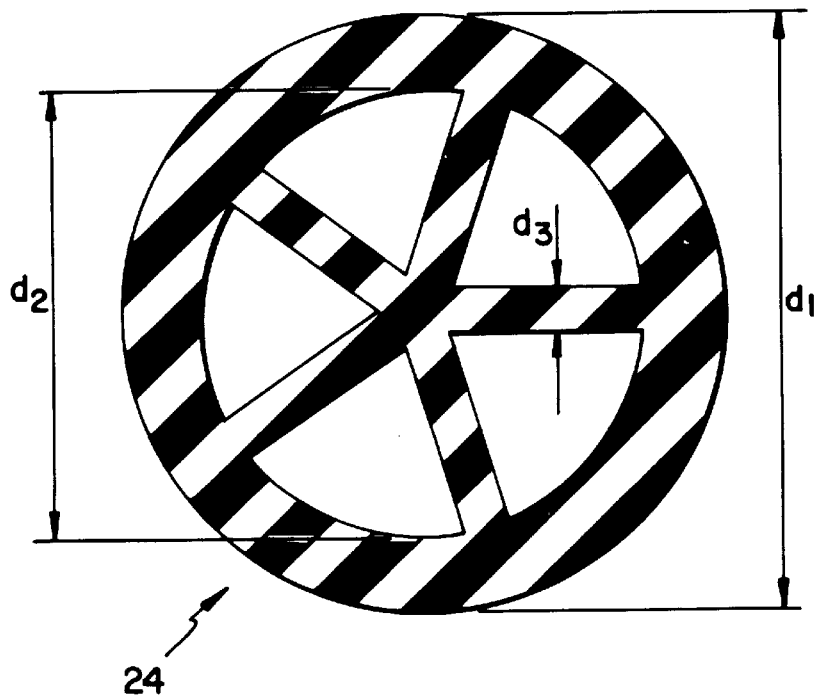
FIG. 2 is a cross-section through a wheel-shaped supported catalyst.
Figure 3:
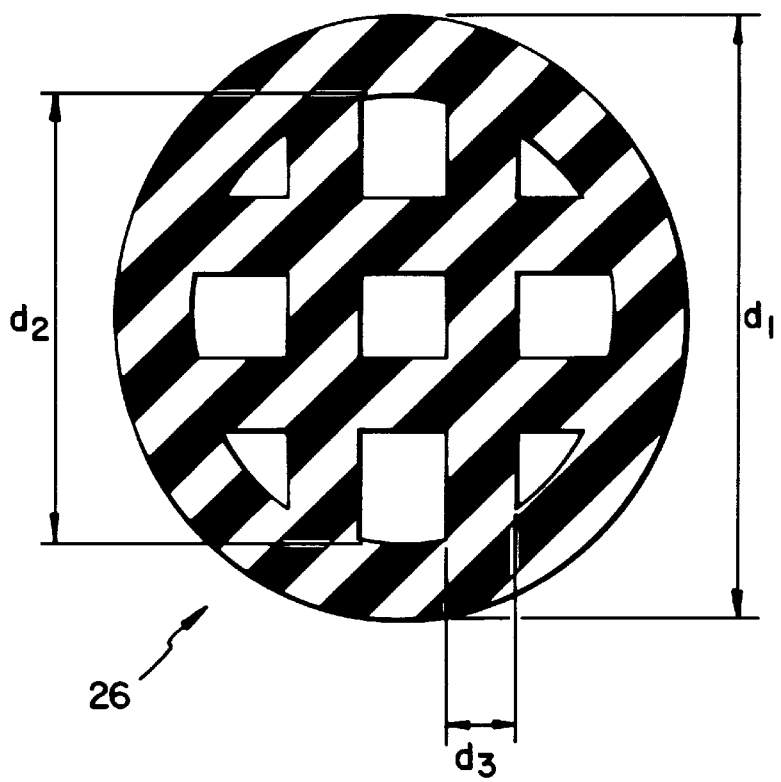
FIG. 3 is a cross-section of a monolith-shaped supported catalyst.
Figure 4:
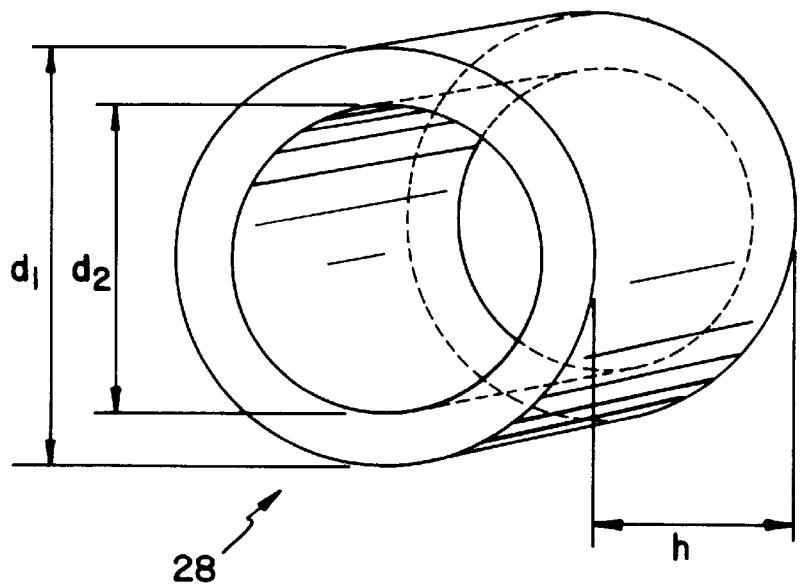
FIG. 4 is a perspective view of the annular hollow extrudate of FIG. 1.
Figure 5:
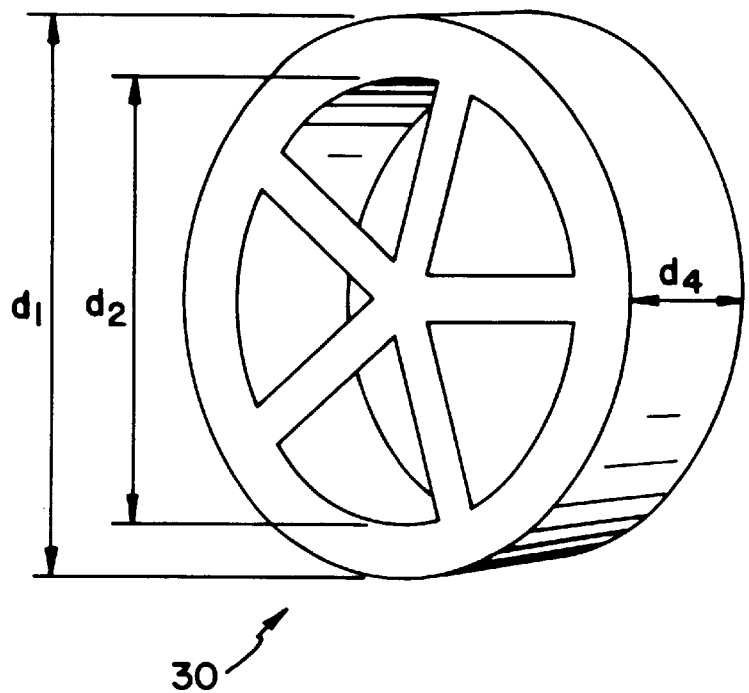
FIG. 5 is a perspective view of the wheel-shaped supported catalyst of FIG. 2.
Figure 6:
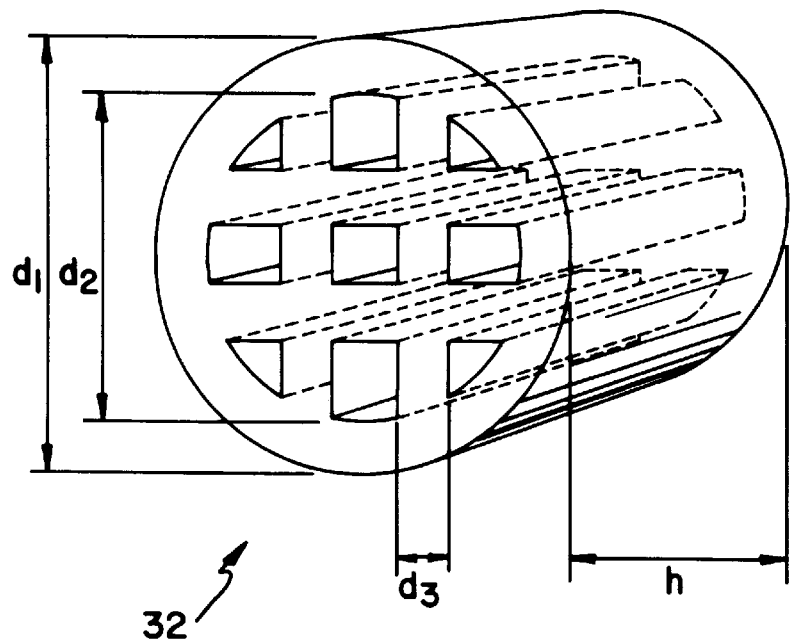
FIG. 6 is a perspective view of the monolith-shaped supported catalyst of FIG. 3.

Each of the Figures refers to an embodiment according to the invention.

DETAILED DESCRIPTION OF THE PREFERRED EMBODIMENTS

With reference to FIGS. 1–6, in which like numerals represent like parts, preferably the external diameter $d_1$ of the wheel-shaped bodies 24, 30 and monolithic shaped bodies 26, 32 is 8 to 10 mm. For the internal diameter $d_2$ preferred values in the case of hollow extrudates 22, 28 are in the range from 1 to 2 mm, and in the case of wheel-shaped bodies 24, 30 and monolithic shaped bodies 26, 32 are in the range from 6 to 8 mm. The spoke thickness or web thickness $d_3$ of wheel-shaped bodies 24, 30 and monolithic shaped bodies 26, 32 is preferably 1 to 1.5 mm. The preferred height h of the moldings is in the range from 3 to 5 mm. The equivalent diameter $d_{eq}$ is calculated according to the formula $d_{eq}=2r$, the relationship $\gamma=(V/\pi \times h)^{1/2}$ applying, where V=volume of the shaped body.

The invention is described in more detail hereinafter with the aid of the following described examples, reference being made to FIG. 7.

EXAMPLE 1

The support materials listed in Table 1 are used. These support materials are packed into 150×150 mm size nickel frames covered with gas-permeable nickel wire meshing on both sides, in a packing height of in each case 50 mm. The nickel pockets filled with the respective support materials are inserted into the upper cap region, filled with ceramic saddle packings, of the second of a total of three oxychlorination reactors connected in series, in such a way that the 230° C. gas stream from the lower part of the upstream first oxychlorination reactor—substantially comprising the reaction products 1,2-dichloroethane and water in the vapor state as well as unreacted hydrogen chloride, ethylene, oxygen and nitrogen from the air fed to the first reactor and from air for the second reactor—flows uncooled through the pockets. Since the support material does not contain any active component, no oxychlorination reaction takes place, with the result that the heating action on the support material proceeds almost isothermally.

recognizable temperature-stabilizing effect (supports A, B, C and supports G, N). The temperature stabilizers known from the literature, such as the oxides of lanthanum, cerium and samarium, produce under comparable conditions only a moderate thermal stability of the support material gamma-aluminum oxide (supports D, E, F, J, K, M), whereas the temperature stabilizer cerium dioxide/zirconium dioxide according to the invention imparts the best thermal stability to gamma-aluminum oxide (supports H, L, O), neither a dependence on the $h/d_{eq}$ value nor on the porosity being detectable when using the claimed shaped bodies. It is surprising however that the preferred thermal stabilizer according to the invention, namely cerium dioxide/zirconium dioxide, does not even achieve the effect of the lanthanum rare earth oxides in the case of columnar and spherical supports (supports P, Q).

This may, without raising doubts about the correctness of the clarification experiment, indicate that the thermal stability does not depend on the thickness of the shaped bodies or their shaped elements, as is generally accepted for the mechanical strength. Instead, the thermal stability is influenced more by other factors, for example an advantageous heat dissipation as a result of the geometry and thermal conductivity.

To summarize, the relative percentage thermal stability of the claimed shaped bodies in the form of hollow cylinders, wheel-shaped bodies and monolith bodies is shown in the following gradation.

TABLE 1

Characteristic Data of the shaped catalyst support based on gamma-aluminium oxide used in Example 1

| Catalyst identification | Catalyst shape | External diameter (mm) | Internal diameter (mm) | Height h (mm) | Spoke or Web-thickness (mm) | Volume of Support (mm³) | $d_e$ (mm) | $h/d_e$ | Pore Volume (cm³/g) | Temperature stabilised (wt. % referred to $\gamma$-Al$_2$O$_3$) |
|---|---|---|---|---|---|---|---|---|---|---|
| A | Hollow cylinder | 4.5 | 1.5 | 4 | — | 56.6 | 4.24 | 0.94 | 0.8 | — |
| B | Wheel shape | 8.5 | 6.3 | 4 | 1.2 | 170 | 7.36 | 0.54 | 0.8 | — |
| C | Monolith | 8.5 | 6.5 | 4 | 1.0 | 177 | 7.51 | 0.53 | 0.8 | — |
| D | Hollow cylinder | 5 | 1.5 | 10 | — | 179 | 4.77 | 2.10 | 0.6 | 5.5% La$_2$O$_3$ |
| E | Hollow cylinder | 5 | 1.5 | 4 | — | 71.5 | 4.77 | 0.84 | 0.6 | 5.5% Sm$_2$O$_3$ |
| F | Hollow cylinder | 5 | 1.5 | 10 | — | 179 | 4.77 | 2.10 | 0.6 | 5.5% CeO$_2$ |
| G | Hollow cylinder | 5 | 1.5 | 10 | — | 179 | 4.77 | 2.10 | 0.6 | 5.5% ZrO$_2$ |
| H | Hollow cylinder | 5 | 1.5 | 10 | — | 179 | 4.77 | 2.10 | 0.6 | 5.0% CeO$_2$ + 0.5% ZrO$_2$ |
| J | Wheel shape | 8 | 4.8 | 8 | 1.6 | 400 | 7.98 | 1.00 | 0.5 | 7.0% La$_2$O$_3$ |
| K | Wheel shape | 8.5 | 6.3 | 4 | 1.2 | 170 | 7.36 | 0.34 | 0.5 | 10.0% CeO$_2$ |
| L | Wheel shape | 8.5 | 4.8 | 8 | 1.6 | 400 | 7.98 | 1.00 | 0.5 | 5.0% CeO$_2$ + 0.5% ZrO$_2$ |
| M | Monolith shape | 8.5 | 6.5 | 8 | 1.0 | 354 | 7.51 | 1.10 | 0.6 | 4.0% Sm$_2$O$_3$ |
| N | Monolith shape | 8.5 | 6.3 | 4 | 1.2 | 170 | 7.36 | 0.54 | 0.6 | 10% ZrO$_2$ |
| O | Monolith shape | 8.5 | 6.3 | 4 | 1.2 | 170 | 7.36 | 0.54 | 0.6 | 7.0% CeO$_2$ + 1.0% ZrO$_2$ |
| P | Column | 5 | — | 5 | — | 98.2 | 5.00 | 1.00 | 0.8 | 5.0% CeO$_2$ + 0.5% ZrO$_2$ |
| Q | Spheres | 4 | — | 4 | — | 33.5 | 3.27 | 1.22 | 0.8 | 9.0% CeO$_2$ + 1.6% ZrO$_2$ |

The fracture hardness of the individual support materials (expressed in Newtons N) was determined before the heat treatment. After one year's exposure to the effect of heat under hydrothermal conditions at 230° C. and a pressure of 6.5 bar absolute the sample pockets are removed and the fracture hardness of the individual support samples is remeasured, the decrease in the fracture hardness being a measure of the temperature stability of the support materials.

The results of these temperature stability investigations are shown in Table 2. From Table 2 it is clear that supports of the claimed geometrical shape without the addition of temperature stabilizers and independently of the $h/d_{eq}$ value as well as of the porosity are the least temperature stable, and the addition of zirconium dioxide does not produce any

| | |
|---|---|
| gamma-aluminum oxide + cerium/zirconium dioxide | 100% |
| gamma-aluminum oxide + lanthanum oxide or cerium dioxide or samarium oxide | 57% |
| gamma-aluminum oxide + zirconium oxide and/or without thermal stabilizer | 38% |

Columnar and spherical supports with addition of cerium dioxide/zirconium dioxide have on the other hand only half the thermal stability compared to the claimed support shapes with additions of cerium dioxide/zirconium dioxide.

TABLE 2

Evaluation of resistance of support materials according to Table 1 on the basis of the change in fracture hardness

| Support material | Fracture hardness (in N) Before | Fracture hardness (in N) After | Loss of fracture hardness due to action of heat (in %) |
|---|---|---|---|
| A | 23 | 10 | 57 |
| B | 44 | 22 | 50 |
| C | 36 | 17 | 53 |
| D | 26 | 16 | 38 |
| E | 23 | 15 | 35 |
| F | 26 | 15 | 42 |
| G | 26 | 12 | 54 |
| H | 26 | 20 | 23 |
| J | 44 | 29 | 34 |
| K | 44 | 30 | 32 |
| L | 44 | 36 | 18 |
| M | 40 | 27 | 32 |
| N | 40 | 19 | 53 |
| O | 40 | 32 | 20 |
| P | 55 | 33 | 40 |
| Q | 60 | 35 | 42 |

EXAMPLE 1a

Support materials having the claimed geometrical shapes and with added cerium/zirconium are treated by impregnating in each case 4000 g of γ-aluminum oxide in the form of hollow cylinders or wheel-shaped or monolith bodies with an aqueous, acetic acid solution of Ce(II) acetate and zirconium(II) acetate according to the specified addition proportions of 5% Ce and 0.5% Zr referred to the support weight, the amount of aqueous solution being such that all the solution is absorbed by the γ-aluminum oxide. The impregnated shaped bodies are then heat treated at 550° C. in a stream of air, whereby a dehydration takes place with conversion of the impregnating salts into oxidic species and support materials of the claimed geometrical shape and having the following composition are formed:

94.5 wt. % $Al_2O_3$
5.0 wt. % $CeO_2$
0.5 wt. % $ZrO_2$

From these temperature-stabilized supports supported catalysts having the claimed shapes and additives are produced in four different formulations that take into account the charging pattern of the three-stage oxychlorination reactor (Example III in Table Ia).

Type A 300 g of temperature-stabilized supports are impregnated with an aqueous solution of 33.91 g of $CuCl_2.2H_2O$ and 13.44 g of KCl and dried at 135° C. Chemical composition of the Type A catalyst after drying:

83.31 wt. % $Al_2O_3$
4.4 wt. % $CeO_2$
0.44 wt. % $ZrO_2$
7.9 wt. % $CuCl_2$
3.95 wt. % KCl

Type B 300 g of temperature-stabilized supports are impregnated with an aqueous solution of 54.08 g of $CuCl_2.2H_2O$ and 12.8 g of KCl and dried at 135° C. Chemical composition of the Type B catalyst after drying:

79.76 wt. % $Al_2O_3$
4.22 wt. % $CeO_2$
0.42 wt. % $ZrO_2$
12.00 wt. % $CuCl_2$
3.60 wt. % KCl

Type C 300 g of temperature-stabilized supports are impregnated with an aqueous solution of 113.52 g of $CuCl_2.2H_2O$ and 8.36 g of KCl and dried at 135° C. Chemical composition of the Type C catalyst after drying:

71.26 wt. % $Al_2O_3$
3.76 wt. % $CeO_2$
0.38 wt. % $ZrO_2$
22.50 wt. % $CuCl_2$
2.10 wt. % KCl

Type D 300 g of temperature-stabilized supports are impregnated with an aqueous solution of 115.46 g of $CuCl_2.2H_2O$ and 15.25 g of KCl and dried at 135° C. Chemical composition of the Type D catalyst after drying:

69.77 wt. % $Al_2O_3$
3.69 wt. % $CeO_2$
0.37 wt. % $ZrO_2$
22.50 wt. % $CuCl_2$
3.75 wt. % KCl

Catalysts of the following composition which were produced using an aqueous solution according to the previously described impregnating procedure were used as reference catalysts. In this case however γ-$Al_2O_3$ support materials that were not temperature stabilized were used.

Chemical composition of the catalysts according to Example I in Table Ia

Type A: 7.9 wt. % $CuCl_2$; 3.95 wt.-% KCl; 88.15 wt.-% $Al_2O_3$
Type B: 12.0 wt.-% $CuCl_2$; 3.60 wt.-% KCl; 84.40 wt.-% $Al_2O_3$
Type C: 22.5 wt.-% $CuCl_2$; 2.10 wt.-% KCl; 75.4 wt.-% $Al_2O_3$
Type D: 22.5 wt.-% $CuCl_2$; 3.75 wt.-% KCl; 73.75 wt.-% $Al_2O_3$ The catalysts according to Example II in Table Ia were additionally impregnated with the addition of $YCl_3.6H_2O$. They have the following chemical composition after drying:

Type A: 7.9 wt.-% $CuCl_2$; 3.95 wt.-% KCl; 0.12 wt.-% $YCl_3$; 88.03 wt.-% $Al_2O_3$
Type B: 12.0 wt.-% $CuCl_2$; 3.6 wt.-% KCl; 0.44 wt.-% $YCl_3$; 83.96 wt.-% $Al_2O_3$
Type C: 22.5 wt.-% $CuCl_2$; 2.1 wt.-% KCl; 0.82 wt.-% $YCl_3$; 74.58 wt.-% $Al_2O_3$
Type D: 22.5 wt.-% $CuCl_2$; 3.75 wt.-% KCl; 0.82 wt.-% $YCl_3$; 72.93 wt.-% $Al_2O_3$ The previously described catalysts were placed according to the corresponding charging gradation in the tube of the first reactor of an air oxychlorination unit employing a three-reactor technology (detailed description in Example 2). The catalysts were removed after 12 months.

The visual evaluation of the removed catalysts according to Table IIa clearly shows the temperature-/shape-stabilising effect of the Ce/Zr addition. The catalysts according to Example I and II that were not temperature stabilised decomposed into dust in zones 2–4. In the case of catalysts prepared with Ce/Zr oxides only a decomposition into coarse and fine particles was observed over the total zone region under a comparable operating time. The addition of yttrium chloride alone did not produce any temperature/shape stabilisation effect.

TABLE Ia

Catalysts for determining the thermal stability according to Example Ia under the operating conditions of the first reactor of an air oxychlorination unit using a three-reactor technique

| Catalyst identification | Catalyst shape | External diameter (mm) | Internal diameter (mm) | Height (mm) | Pore volume (ml/g) | Additives (wt. %) referred to support |
|---|---|---|---|---|---|---|
| I | Hollow cylinder | 4.5 | 1.5 | 7–15 | 0.6 | No addition |
| II | Wagon-wheel | 8.5 | 6.3 | 5 | 0.6 | Addition of $YCl_3$, type dependent |
| III | Wagon-wheel | 8.5 | 6.3 | 5 | 0.6 | 5 Wt. % $CeO_2$ 0.5 wt. % $ZrO_2$ |

TABLE IIa

Thermal stability of the catalysts according to Table I and Example 1a under the operating conditions of the first reactor of an air oxychlorination unit using a three-reactor technique. Visual evaluation after removal of the catalysts (12 months' operation)

| Catalyst Types | Reactor zone 1 Type A | Reactor zone 2 Type A | Reactor zone 3 Type B | Reactor zone 4 Type C | Reactor zone 5 Type C |
|---|---|---|---|---|---|
| I | Coarse and fine fracture | Fine fracture, high proportion of dust | Fine dust | Fine dust | coarse fracture |
| II Bulk density [g/l] | Coarse and fine fracture 855 | Fine dust 1110 | Fine dust 1030 | Fine dust 1060 | Coarse and fine fracture 850 |
| III Bulk density [g/l] | | | Coarse and fine fracture 890 | | |

EXAMPLE 2

Support materials of the claimed geometrical shape are prepared by impregnating in each case 4000 g of gamma-aluminium oxide in the form of hollow cylinders or of wheel or monolith shape having the characteristic data listed in Table 3, with an aqueous solution of 477.5 g of cerium-IV nitrate and 39.7 g of zirconyl dinitrate, the amount of the aqueous solution being such that the whole solution is absorbed by the gamma-aluminium oxide. The impregnated shaped bodies are then heat treated at 150° C. in a stream of air, dehydration taking place with the release of oxygen and nitrogen oxide gases, and support materials of the claimed geometrical shape and having the following composition are obtained:

94.5 Wt.-% $\gamma$-$Al_2O_3$
5.0 Wt.-% $CeO_2$
0.5 Wt.-% $ZrO_2$

From this temperature-stabilised support material supported catalysts having the claimed shape according to Table 3 are charged with the active components according to Table 4, each of the supported catalysts identified from R to Z being produced in the types A, B, C, D.

Type A

In each case 300 g of temperature-stabilised supported catalyst are impregnated with an aqueous solution of 34.19 g of $CuCl_2.2H_2O$, 13.49 g of KCl and 1.54 g of $YCl_3.6H_2O$ and dried at 135° C.

Chemical composition of the Type A supported catalyst after drying:

83.02 Wt.-% $Al_2O_3$
4.4 Wt.-% $CeO_2$
0.44 Wt.-% $ZrO_2$
7.9 Wt.-% $CuCl_2$
3.95 Wt.-% KCl
0.29 Wt.-% $YCl_3$

Type B

In each case 300 g of temperature-stabilised supported catalyst are impregnated with an aqueous solution of 54.36 g of $CuCl_2.2H_2O$, 12.86 g of KCl and 2.44 g of $YCl_3.6H_2O$ and dried at 135° C.

Chemical composition of the Type B supported catalyst after drying:

79.34 Wt.-% $Al_2O_3$
4.20 Wt.-% $CeO_2$
0.42 Wt.-% $ZrO_2$
12.00 Wt.-% $CuCl_2$
3.60 Wt.-% KCl
0.44 Wt.-% $YCl_3$

Type C

In each case 300 g of temperature-stabilised supported catalysts are impregnated with an aqueous solution of 114.73 g of $CuCl_2.2H_2O$, 8.45 g of KCl and 5.13 g of $YCl_3.6H_2O$ and dried at 135° C.

Chemical composition of the Type C supported catalyst after drying:

70.48 Wt.-% $Al_2O_3$
3.73 Wt.-% $CeO_2$
0.37 Wt.-% $ZrO_2$
22.50 Wt.-% $CuCl_2$
2.10 Wt.-% KCl
0.82 Wt.-% $YCl_3$

Type D

In each case 300 g of temperature-stabilised supported catalyst are impregnated with an aqueous solution of 117.33 g of $CuCl_2.2H_2O$, 15.43 g of KCl and 5.23 g of $YCl_3.6H_2O$ and dried at 135° C.

Chemical composition of the Type D supported catalyst after drying:

68.92 Wt.-% $Al_2O_3$
3.65 Wt.-% $CeO_2$
0.36 Wt.-% $ZrO_2$
22.50 Wt.-% $CuCl_2$
3.75 Wt.-% KCl
0.82 Wt.-% $YCl_3$

TABLE 3

Characteristic data of the supported catalysts used in Example 2 based on gamma aluminium oxide, mixed with 5 wt. % of cerium dioxide and 0.5 wt. % of zirconium dioxide, in each case referred to gamma-aluminium dioxide

| Catalyst identification | Catalyst shape | External diameter | Internal diameter (mm) | Height h (mm) | Spoke or web-thickness (mm) | Volume of Support (mm³) | $d_e$ (mm) | $h/d_e$ | Pore-Volume (cm³/g) | Proportion of active components |
|---|---|---|---|---|---|---|---|---|---|---|
| R | Wheel Shape | 8.5 | 6.3 | 4 | 1.2 | 170 | 7.36 | 0.54 | 0.8 | see Table 4 |
| S | Wheel shape | 8.5 | 6.3 | 4 | 1.2 | 170 | 7.36 | 0.54 | 0.5 | |
| T | Wheel shape | 8.5 | 4.8 | 8 | 1.2 | 400 | 7.98 | 1.00 | 0.8 | |
| U | Hollow cylinder | 4.5 | 1.5 | 4 | — | 56.6 | 4.24 | 0.94 | 0.8 | |
| V | Hollow cylinder | 5.0 | 1.5 | 4 | — | 71.5 | 4.77 | 0.84 | 0.6 | |
| W | Hollow cylinder | 5.0 | 1.5 | 10 | — | 179 | 4.77 | 2.10 | 0.8 | |
| X | Monolith shape | 8.5 | 6.3 | 4 | 1.2 | 170 | 7.36 | 0.54 | 0.8 | |
| Y | Monolith shape | 8.5 | 6.3 | 4 | 1.2 | 170 | 7.36 | 0.54 | 0.6 | |
| Z | Monolith shape | 8.5 | 6.5 | 8 | 1.0 | 354 | 7.51 | 1.10 | 0.8 | |

TABLE 4

Proportions of active components of the supported catalysts listed in Table 3 and reactor tube filling plan. The following sub-types of each of the supported catalysts according to Table 3 identified by R to Z are used (figures in % by weight in each case refer to the total weight of the supported catalysts).

|  | $CuCl_2$ | KCl | $YCl_3$ |
|---|---|---|---|
| Type A | 7.9 | 3.95 | 0.29 |
| Type B | 12.0 | 3.60 | 0.44 |
| Type C | 22.5 | 2.10 | 0.82 |
| Type D | 22.5 | 3.75 | 0.82 |

The reactor tube filling plan in the first of three oxychlorination reactors connected in series, in which in each case nine of a total of 3200 tubes were charged uniformly over the reactor cross-section with the supported catalysts R to Z according to Table 3, is as follows (from top to bottom, i.e. in the direction of the product flow):

| 1st Zone | Type A | from catalyst R . . . Z |
| 2nd Zone | Type A | from catalyst R . . . Z |
| 3rd Zone | Type B | from catalyst R . . . Z |
| 4th Zone | Type C | from catalyst R . . . Z |
| 5th Zone | Type D | from catalyst R . . . Z |

In the first reactor of an air oxychlorination unit using a three-reactor technique, in which the reactors are cooled by evaporation of hot water, a fresh supported catalyst based on gamma-aluminum oxide without addition of a thermal stabilizer is packed in hollow cylinders having the dimensions according to EP 0 461 431; the supported catalyst is impregnated with copper chloride and potassium chloride in the four types A to D according to Table 4, though without the addition of yttrium-III chloride, the zonal filling plan described in Table 4 being used. Nine of the total number of 3200 reactor tubes are however filled uniformly over the reactor cross-section with the catalyst samples R to Z according to Table 3 and Table 4.

The second and third reactors contain already used but still intact catalysts according to EP 0 461 431. The first reactor is charged with 400 kmole/hr of HCl, 220 kmole/hr of ethylene and 219 kmole/hr of air. A further 219 kmole/hr of air and 109 kmole/hr of air are added to the outflow mixture from the first reactor and from the second reactor.

At a pressure in the system of 6.5 bar absolute, measured at the inlet to the first reactor, and at a steam collecting drum pressure or reactor cooling jacket pressure of 20 bar absolute, the educts are converted to 1,2-dichloroethane and water, the oxygen added together with the air to the first reactor being almost quantitatively consumed. Excess HCl and ethylene together with the reaction products are converted under further addition of air into 1,2-dichloroethane and water in the following reactors. After eight months' operation, in the course of which the pressure of the steam collecting drum of the first reactor had to be successively raised to a value of 29 bar absolute in order to regulate the magnitude and position of the hot-spot temperatures and to compensate the gradual deterioration in activity, there occurred a sudden bed compaction in the first reactor, combined with increasing loss of reaction selectivity, with the result that the unit had to be shut down and the catalyst had to be changed. On emptying the reactor it was found that the commercial catalysts according to EP 0 461 431 had decomposed in all zones almost to dust or coarse and fine-grain particles, the predominant phase being α-aluminum oxide with only a small amount of gamma-aluminum oxide phase remaining.

The nine incorporated and marked catalyst samples according to Table 3 and Table 4 were removed by suction zone by zone and individually investigated. The results are summarized in Table 5.

The results demonstrate that the supported catalysts (catalyst samples R, U and X according to Table 3 and Table 4) having the combination of the four features according to the invention exhibit a good resistance to the prolonged action of elevated temperatures under oxychlorination conditions, i.e. release of heat of reaction at the catalyst particles. After eight months' exposure to the effect of high temperatures the loss of fracture hardness was on average only 24% referred to the initial values, whereas the catalyst samples S, T, V, W, Y, Z—as recorded in Table 6—suffered, due to non-fulfillment of the combined feature of porosity and $h/d_{eq}$ value, on average a 62% deterioration in the fracture hardness in the same period compared to the catalyst samples according to the invention under comparable temperature and reaction conditions, the loss in fracture hardness being on average 39% referred to the respective initial values. This is surprising since the results of Example 1 according to Table 2 demonstrate that merely the addition of the temperature stabilizer mixture cerium dioxide/ zirconium dioxide according to the invention to the gamma-aluminum oxide support imparts a considerable dimensional stability and thermal stability. It is obvious however that under the conditions of the oxychlorination reaction, in which a considerable heat of reaction is released at various points on the catalyst particles, in addition to the heat supplied through the reactants and reaction products, for a good temperature stability it is necessary that in addition thermo-dynamically as well as reaction kinetically advantageous short diffusion paths are also present in the region of the actual catalytic reaction zone. In particular, it is necessary to prevent as far as possible coking due to the formation of hot spots, which again have an overall adverse effect on the thermal stability despite the presence of temperature stabilizers and reduce the fracture hardnesses due to the increased formation of the α-aluminum oxide phase. Thus, due to the destructive action of the coke inclusions there is a relatively rapid decomposition of the catalyst moldings, even though the latter, due to their shapes according to the invention, promote the heat exchange coefficient between the catalyst body and product gas stream and thus actually facilitate an optimum heat dissipation in the product stream.

TABLE 5

Thermal stability of supported catalysts according to Table 3 and Table 4 under the operating conditions of the first reactor of an air oxychlorination using a three-reactor technique

| Catalyst identification | Reactor 1 | Fracture hardness (N) before | Fracture hardness (N) after | Fracture hardness loss (%) | $\gamma$-Al$_2$O$_3$ | $\alpha$-Al$_2$O$_3$ | Colour | Fracture | Dust | Coking |
|---|---|---|---|---|---|---|---|---|---|---|
| R | Zone 1 | 44 | 36 | 18 | +++ | − | brown | − | − | − |
|  | Zone 2 | 44 | 33 | 25 | +++ | + | brown/grey | + | + | + |
|  | Zone 3 | 44 | 34 | 23 | +++ | − | brown/grey | + | + | + |
|  | Zone 4 | 44 | 33 | 25 | +++ | + | brown/grey | + | + | + |
|  | Zone 5 | 44 | 36 | 18 | +++ | − | brown | + | − | − |
| U | Zone 1 | 26 | 21 | 19 | +++ | − | brown | − | − | − |
|  | Zone 2 | 26 | 18 | 31 | +++ | + | brown/grey | + | + | + |
|  | Zone 3 | 26 | 19 | 27 | +++ | + | brown/grey | − | + | + |
|  | Zone 4 | 26 | 18 | 31 | +++ | + | brown/grey | + | + | + |
|  | Zone 5 | 26 | 20 | 23 | +++ | − | brown | + | − | − |
| X | Zone 1 | 40 | 32 | 20 | +++ | − | brown | − | − | − |
|  | Zone 2 | 40 | 30 | 25 | +++ | + | brown/grey | + | + | + |
|  | Zone 3 | 40 | 31 | 23 | +++ | − | brown/grey | − | + | + |
|  | Zone 4 | 40 | 29 | 28 | +++ | + | brown/grey | + | + | + |
|  | Zone 5 | 40 | 31 | 23 | +++ | − | brown | + | − | − |

+++ Large proportion/
++ moderate proportion/
+ small proportion/
− not detectable

TABLE 6

Thermal stability of supported catalysts according to Table 3 and Table 4 under the operating conditions of the first reactor of an air oxychlorination using a three-reactor technique

| Catalyst identification | Reactor 1 | Fracture hardness (N) before | Fracture hardness (N) after | Fracture hardness - loss (%) | $\gamma$-Al$_2$O$_3$ | $\alpha$-Al$_2$O$_3$ | Colour | Fracture | Dust | Coking |
|---|---|---|---|---|---|---|---|---|---|---|
| S/T | Zone 1 | 44 | 30 | 32 | +++ | + | brown/grey | ++ | + | + |
|  | Zone 2 | 44 | 27 | 39 | +++ | +++ | black | +++ | +++ | +++ |
|  | Zone 3 | 44 | 29 | 34 | +++ | ++ | brown/black | ++ | ++ | ++ |
|  | Zone 4 | 44 | 28 | 36 | +++ | ++ | black | +++ | +++ | +++ |
|  | Zone 5 | 44 | 29 | 39 | +++ | ++ | brown/black | ++ | ++ | ++ |
| V/W | Zone 1 | 26 | 16 | 38 | +++ | + | brown/black | ++ | ++ | ++ |
|  | Zone 2 | 26 | 13 | 50 | +++ | ++ | black | +++ | +++ | +++ |
|  | Zone 3 | 26 | 15 | 42 | +++ | + | black | +++ | +++ | +++ |
|  | Zone 4 | 26 | 14 | 46 | +++ | ++ | black | +++ | +++ | +++ |
|  | Zone 5 | 26 | 16 | 38 | +++ | ++ | brown/black | ++ | ++ | ++ |
| Y/Z | Zone 1 | 40 | 27 | 33 | +++ | + | brown/grey | ++ | + | + |
|  | Zone 2 | 40 | 24 | 40 | +++ | +++ | black | +++ | +++ | +++ |
|  | Zone 3 | 40 | 25 | 38 | +++ | ++ | brown/black | ++ | ++ | ++ |
|  | Zone 4 | 40 | 24 | 40 | +++ | ++ | black | +++ | +++ | +++ |
|  | Zone 5 | 40 | 26 | 35 | +++ | ++ | brown/black | ++ | ++ | ++ |

+++ Large proportion/
++ moderate proportion/
+ small proportion/
− not detectable

EXAMPLE 3 (Comparison Example 1)

Figure 7:
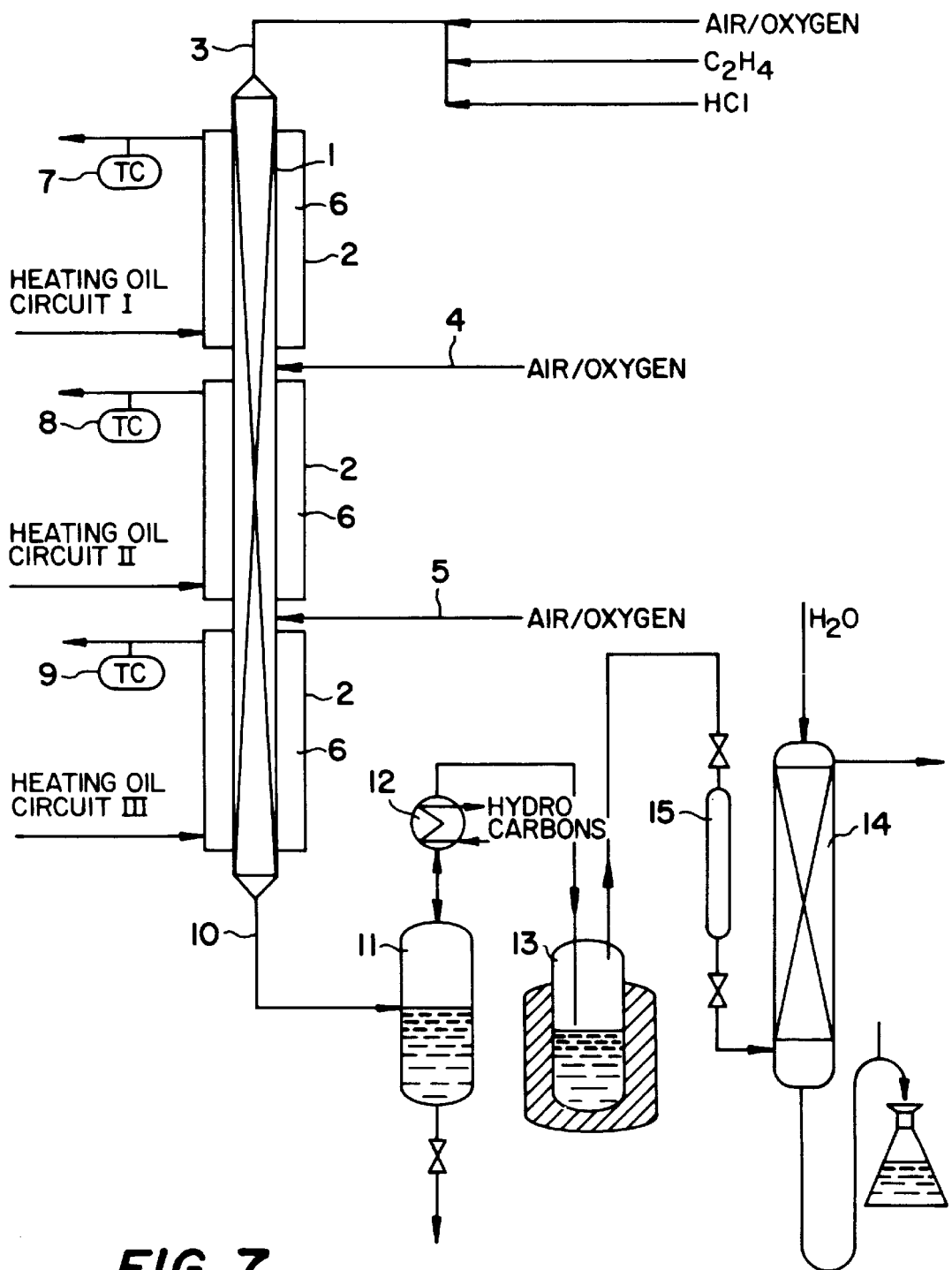
FIG. 7 is a schematic diagram of an oxychlorination process.

Similarly to Example 2, the catalyst samples R, U and Z according to Table 3—though in each case without the addition of the temperature stabilizer cerium dioxide/zirconium dioxide—are charged with the active components according to Table 4 and packed according to the same filling plan into three tubes distributed uniformly over the cross-section of the first reactor as shown in FIG. 7, while the remaining 3197 tubes are filled with catalysts according to EP 0 461 431. The reaction conditions and the loading of the reactor unit are similar to Example 2. After only six months the catalyst in the first reactor had to be replaced on account of the increasing pressure drop. The sample catalysts removed by suction from the three sample tubes exhibited significant signs of fracture in all five zones, with the formation of a large amount of coarse and fine dust as well as substantial amounts of coking, above all in the region of the two camel hump-shaped axial hot spot zones. The addition of yttrium-III chloride by itself therefore does not produce a temperature-stabilizing effect, despite the presence of thermodynamically and reaction kinetically advantageous short diffusion paths produced by the individual features of porosity and $h/d_{eq}$ value according to the invention, and despite the optimum heat dissipation due to the claimed shape geometries.

EXAMPLE 4

The laboratory reactor that is used consists according to FIG. 7 of a vertical nickel tube 1 of internal diameter 25 mm and length 2000 mm and surrounded by a steel jacket 2. The reactor has three feed inlets, the inlet point 3 being arranged at the upper end of the reaction tube, while the inlet points 4 and 5 are arranged laterally after the first third and second third of the reaction tube.

Thermostatically controlled silicone oil is pumped at different temperatures in three heating/cooling circuits I to II in the hollow space 6 between the nickel tube 1 and steel tube 2, which is subdivided vertically into three equally long segments.

The three circuits I to III can in each case be separately controlled as regards temperature via the regulating elements 7, 8, 9. The reaction tube is charged in each case with the supported catalysts R to Z according to Table 3 and Table 4 according to the following filling plan (viewed from top to bottom):

130 mm Berl saddle (inert material) of 4 mm diameter
235 mm catalyst R to Z, in each case type A, containing 7.9 wt. % $CuCl_2$, 3.95 wt. % KCl and 0.29 wt. % $YCl_3$
115 mm catalyst R to Z, in each case type B, containing 12.0 wt. % $CuCl_2$, 3.6 wt. % KCl and 0.44 wt. % $YCl_3$.
115 mm catalyst R to Z, in each case type C, containing 22.5 wt. % $CuCl_2$, 2.1 wt. % KCl and 0.82 wt. % $YCl_3$.
115 mm catalyst R to Z, in each case type D, containing 22.5 wt. % $CuCl_2$, 3.75 wt. % KCl and 0.82 wt. % $YCl_3$.
350 mm catalyst R to Z, in each case type B, containing 12.0 wt. % $CuCl_2$, 3.6 wt. % KCl and 0.44 wt. % $YCl_3$.
230 mm catalyst R to Z, in each case type C, containing 22.5 wt. % $CuCl_2$, 2.1 wt. % KCl and 0.82 wt. % $YCl_3$.
580 mm catalyst R to Z, in each case type C, containing 22.5 wt. % $CuCl_2$, 2.1 wt. % KCl and 0.82 wt. % $YCl_3$.
130 mm Berl saddle (inert material) of 4 mm diameter.

The production of the catalysts that are used is described in detail in Example 2. The specific surfaces of the temperature-stabilized supports are between 180 and 250 $m^3/g$. The pore diameter varies largely in the range from 4 to 20 nm. The individual gas flows are fed through calibrated rotameters. 50 Nl/h of hydrogen chloride and 26.5 Nl/h of ethylene are first of all mixed and then passed together with 26 Nl/h of air and/or oxygen through the inlet point 3 to the upper part of the reactor. A further 26 Nl/h of air and/or oxygen and 13 Nl/h of air are added through the inlets 4 and 5. The gaseous reaction mixture leaving the reactor 1 through the line 10 is cooled with water in the cooler 11, resulting in a partial condensation. The liquid phase, consisting of crude 1,2-dichloroethane (EDC) and water, in which unreacted hydrogen chloride is largely dissolved, is separated in the separator 12. The uncondensable gas stream is cooled to 25° C. in the cold trap 13, resulting in further condensation, and is then washed free of hydrogen chloride in the connected water scrubber 14. The two condensates from the separator 12 and the cold trap 13 are combined and analyzed by gas chromatography after separating the aqueous phase by decanting. The waste gas after the cold trap 13 is sampled via the gas sampling device 15 and then investigated by gas chromatography for the determination of CO and $CO_2$.

The hydrogen chloride conversion is calculated from the titrimetrically determined hydrogen chloride content in the combined aqueous phase and in the discharge from the water scrubber 14. The reaction is operated at atmospheric pressure. The results of this experiment are listed in Table 7. The results show that the supported catalysts R, U and X having the combination of the four claimed inventive features are the most active and most selective, recognizable by the higher HCl conversion rates at relatively low reactor temperatures and slight excesses of ethylene and air, in each case referred to the stoichiometric amount of hydrogen chloride, and by the small formation of by-products and low ethylene total oxidation rate at relatively low hot spot temperatures in the first reactor.

As the results of the supported catalysts S, V and Y demonstrate, the activity and selectivity already become significantly worse even if only the individual feature of porosity according to the invention is not fulfilled, which is surprising since normally with a relatively low mesopore fraction and correspondingly reduced pore volume in conjunction with the claimed catalyst dimensioning, the catalytic effectiveness is usually improved. The results of the supported catalysts T, W and Z, in which only the single criterion h/deq according to the invention is not fulfilled, show with a good activity a significant drop in the selectivity, above all as regards the ethylene total oxidation rate.

A person skilled in the art could not have foreseen that the activity- and selectivity-increasing action of yttrium-III chloride is fully manifested only in combination with the claimed features of porosity and h/deq value according to the invention, especially as the literature has already cast doubt on the effect of yttrium-III chloride per se on account of the formation of gas-impermeable oxide films.

EXAMPLE 5 (Comparison Example 2)

The experimental laboratory apparatus described in Example 4 is employed. The following catalysts are used, the filling plan specified in Example 4 being appropriately adopted in each case.

Catalyst 1
Support material: $\gamma$-$Al_2O_3$ with 5 wt. % $CeO_2$ and 0.5 wt. % $ZrO_2$, pore volume 0.8 $cm^3/g$, $h/d_{eq}$=0.5, wheel-shaped body
Type A: with 7.9 wt. % $CuCl_2$, 3.95 wt. % KCl and 0.36 wt. % $LaCl_3$
Type B: with 12.0 wt. % $CuCl_2$, 3.6 wt. % KCl and 0.55 wt. % $LaCl_3$ Type C: with 22.5 wt. % $CuCl_2$, 2.1 wt. % KCl and 1.03 wt. % $LaCl_3$
Type D: with 22.5 wt. % $CuCl_2$, 3.75 wt. % KCl and 1.03 wt. % $LaCl_3$
Catalyst 2
Support material: $\gamma$-$Al_2O_3$ with a pore volume of 0.8 cm$^3$/g, $h/d_{eq}$=0.5, wheel-shaped body
Type A: with 7.9 wt. % $CuCl_2$, 3.95 wt. % KCl and 0.29 wt. % $YCl_3$
Type B: with 12.0 wt. % $CuCl_2$, 3.6 wt. % KCl and 0.44 wt. % $YCl_3$
Type C: with 22.5 wt. % $CuCl_2$, 2.1 wt. % KCl and 0.82 wt. % $YCl_3$
Type D: with 22.5 wt. % $CuCl_2$, 3.75 wt. % KCl and 0.82 wt. % $YCl_3$
Catalyst 3
Support material: $\gamma$-$Al_2O_3$ with a pore volume of 0.8 cm$^3$/g, $h/d_{eq}$=0.5, wheel-shaped body
Type A: with 7.9 wt. % $CuCl_2$, 3.95 wt. % KCl
Type B with 12.0 wt. % $CuCl_2$, 3.6 wt. % KCl
Type C: with 22.5 wt. % $CuCl_2$, 2.1 wt. % KCl
Type D: with 22.5 wt. % $CuCl_2$, 3.75 wt. % KCl The reactor was charged in each case with 50 Nl/h of hydrogen chloride gas. The addition of ethylene and total air is calculated from the stoichiometric excess data given in each case in Table 8, the splitting of the total air among the three reactors being similar to Example 4, i.e. 40/40/20%. Besides details of the respective reaction temperatures and hot spot temperatures in the first reactor, Table 8 also summarizes the experimental results.

The results show that lanthanum-III chloride is somewhat less active compared to yttrium-III chloride (Table 7) at comparable reaction temperatures and excess amounts of ethylene and air, but is significantly less selective, above all with regard to the ethylene total oxidation rate, which rises enormously on account of the generation of a particularly high hot spot temperature in the first reactor. This is attributed to the fact that lanthanum-III chloride, in contrast to yttrium-III chloride, is not the right activator, since although it catalyzes the reaction rate by reducing the activation energy (corresponding to a decrease in temperature in the region of the actual reaction zone of the catalyst), it raises only the pre-exponential factor, whereby although the number of collisions of the reacting molecules is increased (corresponding to a definite increase in activity), hot spots however form on the catalyst particles and greatly impair the selectivity.

The results of the catalysts 2 and 3 demonstrate that the supported catalysts according to the invention without the addition of yttrium-III chloride are less active and selective. In order in fact to achieve a HCl conversion of about 99.5%, in the absence of the promoter yttrium-III chloride it is necessary to raise the reaction temperatures and the amounts of excess ethylene and air. Both these measures lead inevitably to a deterioration in selectivity since elevated temperatures in general promote substitution reactions and cleavage reactions (formation of 1,1,2-trichloroethane and $C_1$ chlorinated hydrocarbons by C-C chain splitting) while elevated ethylene and oxygen partial pressures in the reaction mixture increase the ethylene total oxidation rate, especially on raising the temperature.

TABLE 7

Results of Example 4

| | Cycle-temperatures | | | Ethylene | Air* | HCl | Selectivity to | | | | | Hot Spot in 1st |
| | I | II | III | excess | excess | conversion | EDC | Chloral | Chloroform | Carbon tetra-chloride | 1.1.2-trichloro-ethane | CO* | reactor |
| Catalyst | °C. | °C. | °C. | % | % | % | mole % | mole % | mole % | mol % | mole % | mole % | °C. |
| R | 190 | 200 | 210 | 6 | 9 | 99.5 | 97.4 | 0.02 | 0.03 | 0.03 | 0.2 | 2.2 | 270 |
| S | 190 | 200 | 210 | 6 | 9 | 99.0 | 96.6 | 0.02 | 0.04 | 0.04 | 0.5 | 2.7 | 298 |
| T | 190 | 200 | 210 | 6 | 9 | 99.4 | 96.5 | 0.02 | 0.04 | 0.04 | 0.5 | 2.8 | 300 |
| U | 190 | 200 | 210 | 6 | 9 | 99.3 | 97.2 | 0.02 | 0.03 | 0.03 | 0.3 | 2.3 | 275 |
| V | 190 | 200 | 210 | 6 | 9 | 89.8 | 96.4 | 0.02 | 0.05 | 0.05 | 0.5 | 2.9 | 300 |
| W | 190 | 200 | 210 | 6 | 9 | 99.2 | 96.3 | 0.02 | 0.04 | 0.04 | 0.5 | 3.0 | 302 |
| X | 190 | 200 | 210 | 6 | 9 | 99.4 | 97.3 | 0.02 | 0.03 | 0.03 | 0.2 | 2.3 | 273 |
| Y | 190 | 200 | 210 | 6 | 9 | 89.9 | 96.5 | 0.02 | 0.04 | 0.04 | 0.5 | 2.8 | 299 |
| Z | 190 | 200 | 210 | 6 | 9 | 99.3 | 96.4 | 0.02 | 0.04 | 0.04 | 0.5 | 2.9 | 301 |

*In each case referred to the stoichiometric amount of hydrogen chloride

TABLE 8

Results of Example 5

| | Cycle-temperatures | | | Ethylene | Air* | HCl | Selectivity to | | | | | Hot Spot in 1st |
| | I | II | III | excess | Excess | conversion | EDC | Chloral | Chloroform | Carbon tetra-chloride - | 1.1.2-trichloro-ethane | CO* | reactor |
| Catalyst | °C. | °C. | °C. | % | % | % | mole % | mole % | mole % | mole % | mole % | mole % | °C. |
| 1 | 190 | 200 | 210 | 6 | 9 | 99.0 | 95.0 | 0.08 | 0.04 | 0.04 | 0.4 | 4.3 | 320 |
| 2 | 190 | 200 | 210 | 6 | 9 | 99.5 | 97.4 | 0.02 | 0.03 | 0.03 | 0.2 | 2.2 | 270 |
| 3 | 200 | 210 | 220 | 12 | 18 | 99.0 | 92.0 | 0.16 | 0.08 | 0.10 | 1.1 | 6.4 | 307 |

*in each case referred to the stoichiometric amount of hydrogen chloride

Compared to the results of Table 7 and the catalysts 2 and 3 in Table 8, it can be seen that yttrium-III chloride strongly suppresses the formation of chloral in particular, with the result that much less alkali is consumed for the necessary caustic splitting to chloroform and sodium formate in the alkali wash of the resultant crude EDCs.

EXAMPLE 6

The three-reactor system described in Example 4 and illustrated in FIG. 7 is employed. The supported catalyst R according to the invention of Tables 3 and 4 is used, with the same filling plan as in Example 4. The reaction conditions are likewise the same as Example 4, except that pure oxygen is used instead of air. In order to simulate approximately the technical cycled gas procedure in the ethylene-rich range according to U.S. Pat. No. 3,892,816, on account of the lack of a cycled gas compressor the following amounts of reactants are used:

50 Nl/hr of hydrogen chloride, mixed with 95 Nl/hr of ethylene and
5.3 Nl/hr of oxygen via inlet point 3;
5.3 Nl/hr of oxygen via inlet point 4; and
2.3 Nl/h of oxygen via inlet point 5.

This feed setting corresponds to an oxygen excess of 3.2% and an ethylene excess of 380%, in each case referred to the stoichiometric amount of hydrogen chloride.

The working-up and analytical evaluation of the reaction products are performed according to Example 4.

The following results were obtained at temperatures of

| Circulation I | at 190° C. |
| Circulation II | at 200° C. |
| Circulation II | at 200° C. |

Hot spot temperature in R-301: 252° C.
HCl conversion: 99.8%
Selectivity
98.6 mole % EDC
0.01 mole % chloral
0.02 mole % chloroform
0.02 mole % carbon tetrachloride
0.05 mole % 1,1,2-trichloroethane
1.2 mole % $CO_x$ If the measurement results are compared with those of Example 4 (Table 7), the superior technology of the cycled oxygen gas procedure with a high ethylene content in the cycled gas can clearly be seen, above all as regards the activity and selectivity. Furthermore, on account of the low hot spot temperatures due to the cycled oxygen gas procedure, the thermal resistance and long-term stability of the claimed supported catalysts according to the invention are also significantly improved.

What is claimed is:

1. Supported catalyst comprising:
   a) 0.5–15 wt. % of one or more Cu-II compounds, the quantitative amounts referring to copper metal,
   b) 0.1–8 wt. % of one or more alkali metal compounds, the quantitative amounts referring to alkali metal,
   c) 0.1–10 wt. % of an oxide mixture comprising
      c1) 80–95 mole % of oxides of cerite rare earths with atomic Nos. 57 to 62, except promethium, and
      c2) 5–20 mole % of zirconium dioxide, where c1) and c2) together total 100 mole % and the quantitative amount of c) refers to the oxides of the mixture, and
   d) the remainder up to 100 wt. % comprising at least one member selected from the group consisting of γ-aluminum oxide and α-aluminum oxide as support material, wherein
   e) the support material d) has a total pore volume in a range from 0.65 to 1.2 cm³/g, and wherein
   f) the supported catalyst is present in form of cylindrical hollow bodies having at least one passage channel, a ratio of height h to external diameter $d_e$ of the hollow bodies being less than 1.5 for diameters $d_e$ of up to 6 mm, and the ratio $h/d_e$ being less than 0.6 for diameter $d_e$ greater than 6 mm.

2. A supported catalyst according to claim 1, wherein a molar ratio of Cu-II compounds a) to alkali metal compounds b) is in the range from 1:1 to 8:1.

3. A supported catalyst according to claim 1, comprising 2–8 wt. % of oxide mixture c).

4. A supported catalyst according to claim 1, wherein the oxide mixture c) comprises 80–90 mole % of c1) and 10–20 mole % of c2).

5. A supported catalyst according to claim 1, wherein the Cu-II compound is $CuCl_2$.

6. A supported catalyst according to claim 1, wherein the alkali metal compound is KCl.

7. A supported catalyst according to claim 1, wherein c1) is $CeO_2$.

8. A supported catalyst according to claim 1, wherein d) is γ-$Al_2O_3$.

9. A supported catalyst according to claim 1, wherein 80% of the total pore volume are mesopores with a diameter in a range from 4 to 20 nm.

10. A supported catalyst according to claim 1, wherein the cylindrical hollow bodies comprise at least one member selected from the group consisting of hollow extrudates, wheel-shaped bodies with 2 to 12 spokes and monolith bodies.

11. A supported catalyst according to claim 10, wherein the external diameters of the hollow bodies are in a range from 4 to 10 mm.

12. A supported catalyst according to claim 10, wherein the cylindrical hollow bodies are wheel-shaped bodies or monolith bodies, and wherein $h/d_e \leq 0.6$.

13. A supported catalyst according to claim 1, further comprising a yttrium-III compound.

14. A supported catalyst according to claim 13, comprising 0.5 to 10 mole % of yttrium-III compound, with respect to the molar content of copper-II compound(s).

15. A supported catalyst according to claim 14, wherein the yttrium-III compound is $YCl_3$.

16. A process for producing a supported catalyst according to claim 1 comprising:
   i) charging the support material d) having the form f) with soluble precursor compounds of the components c1) and c2);
   ii) converting the precursor compounds into an oxide form, and
   iii) loading the oxide charged support materials with the components a) and b).

17. A process for producing a supported catalyst according to claim 1, further comprising:
   iv) forming a mixture of the components c) and d) into the form f), and
   v) loading the formed support materials with the components a) and b).

18. A process of using a supported catalyst according to claim 1, comprising:

oxychlorinating ethylene with hydrogen chloride in the presence of the supported catalyst.

19. A process for producing 1,2-dichloroethane comprising:

oxychlorinating ethylene with hydrogen chloride using a supported catalyst according to claim 1, wherein air or oxygen-enriched air or pure oxygen is used as oxidizing agent with cycling of the excess, unreacted ethylene in an ethylene-enriched cycled gas, wherein the process is carried out in at least one stage at a temperature being between 220° C. and 320° C. at a pressure of 3 to 10 bar absolute.

* * * * *